(12) United States Patent  
Corbett et al.

(10) Patent No.: US 8,130,903 B2
(45) Date of Patent: *Mar. 6, 2012

(54) NONDESTRUCTIVE DEVICE AND METHOD FOR EVALUATING ULTRA-HARD POLYCRYSTALLINE CONSTRUCTIONS

(75) Inventors: Loel Corbett, Saratoga Springs, UT (US); Ronald K. Eyre, Orem, UT (US)

(73) Assignee: Smith International, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/567,613

(22) Filed: Sep. 25, 2009

(65) Prior Publication Data

US 2010/0089663 A1   Apr. 15, 2010

Related U.S. Application Data

(63) Continuation-in-part of application No. 11/550,671, filed on Oct. 18, 2006, now Pat. No. 7,864,919.

(60) Provisional application No. 60/728,057, filed on Oct. 18, 2005.

(51) Int. Cl.
   *G01N 23/223* (2006.01)

(52) U.S. Cl. ............................................. 378/44; 378/45

(58) Field of Classification Search .............. 378/44–46, 378/50

See application file for complete search history.

(56) References Cited

U.S. PATENT DOCUMENTS

| 7,302,034 | B2 * | 11/2007 | Grodzins | 378/50 |
| 7,616,734 | B1 * | 11/2009 | Corbett et al. | 378/46 |
| 7,864,919 | B1 * | 1/2011 | Eyre et al. | 378/44 |

* cited by examiner

*Primary Examiner* — Jurie Yun
(74) *Attorney, Agent, or Firm* — Connolly Bove Lodge & Hutz LLP

(57) ABSTRACT

A device, system and method for nondestructively obtaining qualitative and/or quantitative information relating to the material properties of a region in a diamond body comprises directing x-rays onto the body. The body can comprise sintered or unsintered diamond. The body can ultimately be in the form of a cutting element used with a subterranean drill bit. The x-rays penetrate the body and cause a target element within the desired region including the same to emit x-ray fluorescence. The emitted x-ray fluorescence is received and information relating to content, location, and/or distribution of the target element in the region within the body is determined therefrom. The measured region can extend axially or radially from a surface of the body, and the target elements are nondiamond materials that can be constituents of a substrate attached to the body, or of a container used during HPHT sintering of the body.

30 Claims, 6 Drawing Sheets

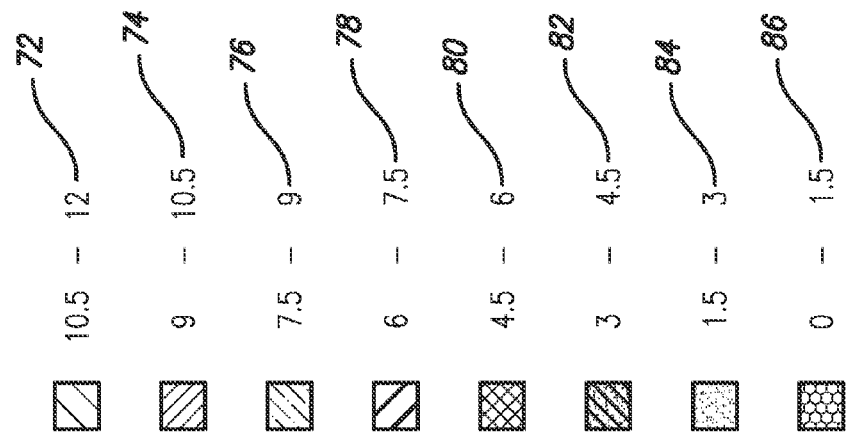
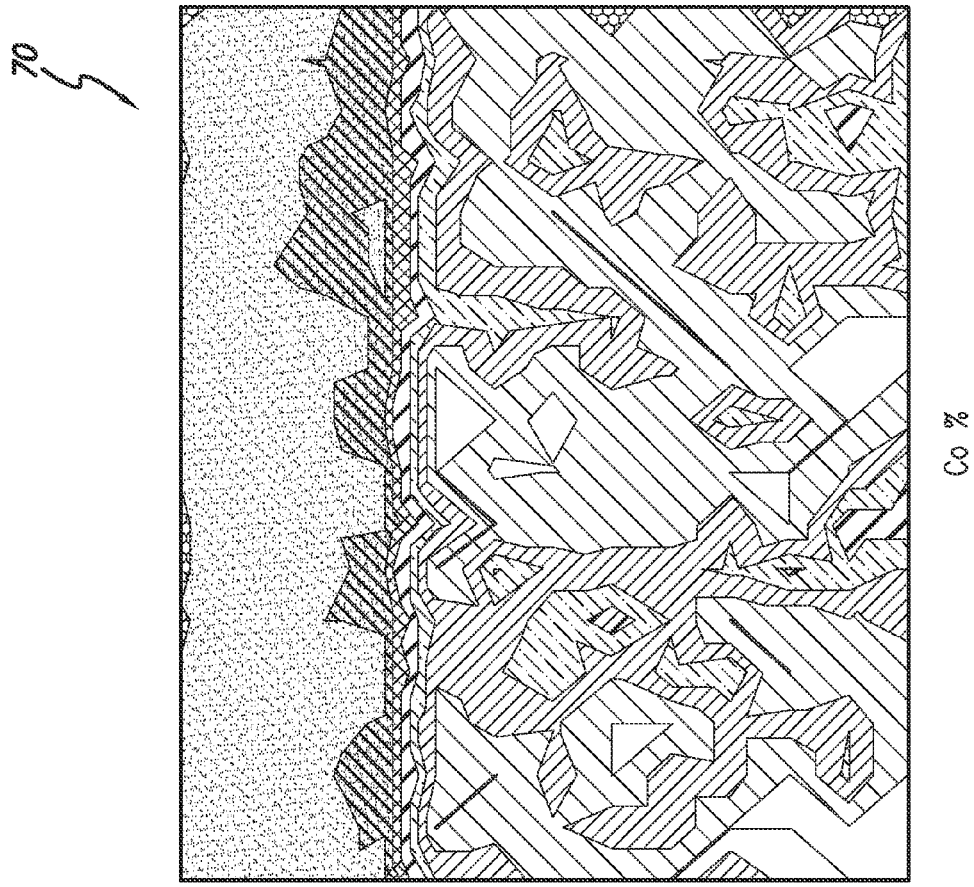
FIG. 7

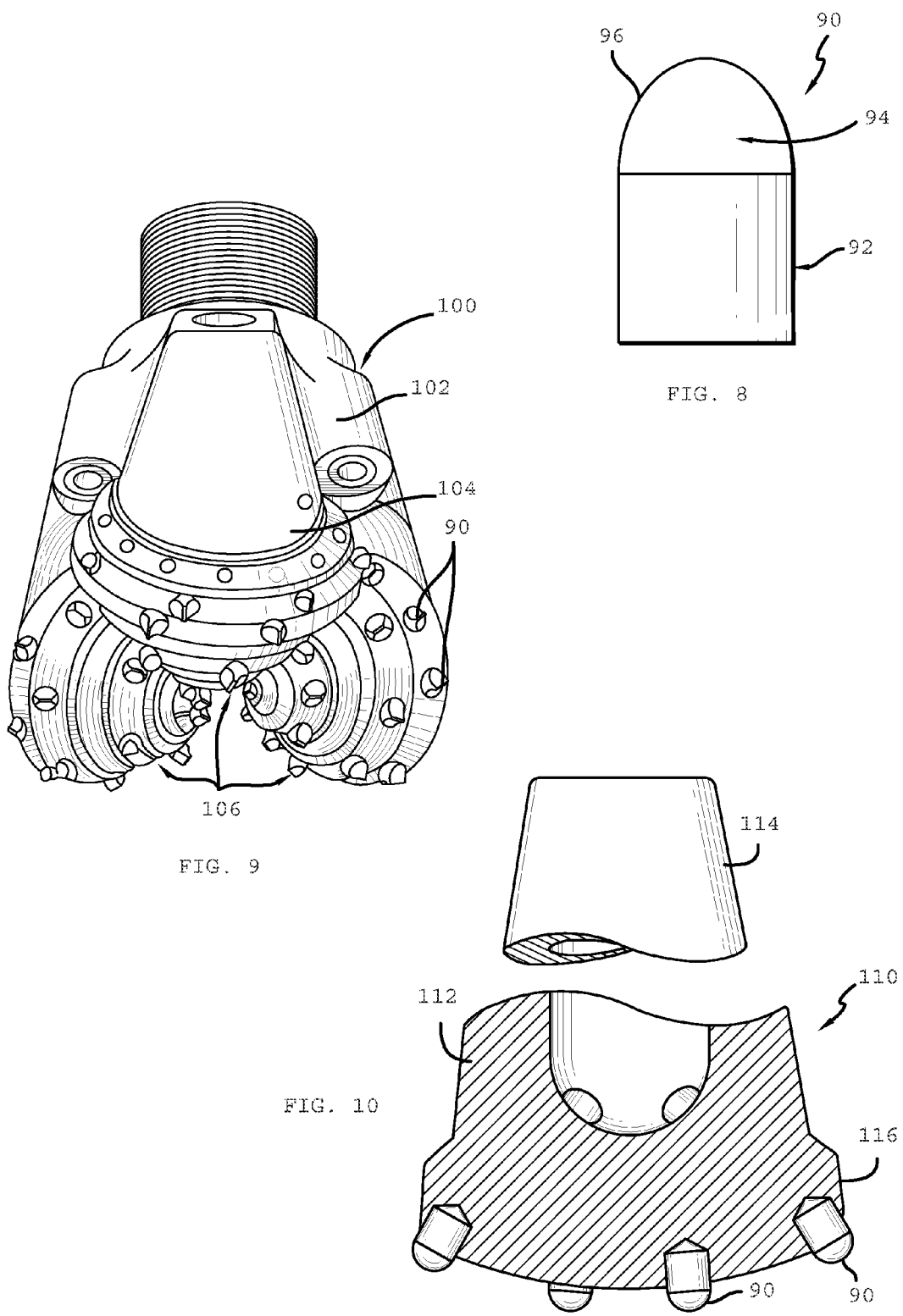

NONDESTRUCTIVE DEVICE AND METHOD FOR EVALUATING ULTRA-HARD POLYCRYSTALLINE CONSTRUCTIONS

RELATION TO COPENDING PATENT APPLICATIONS

This patent application is a continuation-in-part of U.S. patent application Ser. No. 11/550,671 filed on Oct. 18, 2006, now U.S. Pat. No. 7,864,919 that claims priority of U.S. Provisional Patent Application Ser. No. 60/728,057, that was filed on Oct. 18, 2005, and which are both incorporated herein in their entirety by reference.

FIELD OF THE INVENTION

This invention relates to nondestructive devices and methods useful for determining the material content and microstructure of a polycrystalline construction and, more specifically, to using X-ray fluorescence as a technique for providing quantitative and/or qualitative information relating to one or more target materials within one or more selected regions of an ultra-hard polycrystalline construction to thereby provide an indication of the material content and/or material microstructure of the construction and its suitability for a particular end-use application.

BACKGROUND OF THE INVENTION

Ultra-hard constructions comprising a body formed from ultra-hard materials such as polycrystalline diamond (PCD) are well known for their use in abrasive wear and/or cutting applications such as drilling subterranean formations. Conventionally, such PCD bodies are formed/sintered by subjecting a volume of diamond grains to conditions of high pressure-high temperature (HPHT) in the presence of a catalyst material. During this sintering process, the diamond body is oftentimes attached to a metallic substrate, which is useful for both providing the source of the catalyst material to the diamond volume during sintering, and for providing an attachment point for the resulting compact, thereby enabling attachment of the compact to a desired end-use device, e.g., to a drill bit or the like.

It is oftentimes desired that the PCD body be engineered to provide a desired combination of performance properties such as wear resistance, abrasion resistance, fracture toughness, thermal resistance, and impact resistance, making it uniquely suited to a particular end-use application to extend the service life of the body, This combination of performance properties is achieved by the selective choice of materials used to form the PCD body, the amount, location, and/or distribution of such materials within the body, and/or the manner in which the materials are treated or sintered during processing to provide the resulting material microstructure within the body.

In order to ensure that the resulting ultra-hard compact construction as engineered for a particular end-use application is in fact capable of displaying the desired performance properties for such application in a predictable and consistent matter, it is necessary to evaluate the material content and/or microstructure of the construction. Such evaluation is useful for controlling quality of the constructions being formed, and determining the ability of such constructions to perform as expected.

Methods useful for evaluating quantitative and/or qualitative features relating to the ultra-hard construction material content and/or material microstructure will vary depending on the nature of the construction. For ultra-hard material constructions used in tooling, wear, and cutting applications provided in the form of a PCD material, such qualitative and quantitative analysis has typically been provided through the use of destructive method or destructive testing. Destructive testing requires that the construction itself be cut or otherwise treated in a manner that physically exposes the different regions therein so that they can be evaluated and measured by visual inspection.

In an example embodiment, where the construction is one comprising an ultra-hard material such as PCD or cubic boron nitride (cBN), the construction itself is sectioned or cut, e.g., in half, so that the different regions forming the construction can be visually inspected for purposes of evaluating or measuring any variation in material properties in the sectioned region. In an example embodiment, such visual inspection is made with the assistance of a magnifying device such as a microscope, e.g., a scanning electron microscope.

While such destructive analysis and test methods are useful for providing useful certain information relating to the material properties of the sectioned region of the constriction, it is time consuming in that after the part is cut it must usually be further prepared by grinding, polishing or the like, then mounted for microscopic evaluation, and the microscopic evaluation must be taken over a number of different points to gather sufficient data to arrive at a numerical value, e.g., an average region thickness throughout the part. Further, the use of such destructive test method is expensive, and results in the measured parts being destroyed, thereby adversely impacting the economics of making the parts.

Further, this destructive technique is very limited as to the scope of the information gained regarding the material microstructure of the construction, as it only provides insight relating to the material properties of the specific region that's been sectioned. As a result, it provides very little if any information or insight as to the material properties of the remaining regions of the construction, which information would be useful for the purpose of gaining a more thorough understanding of the entire microstructure and the distribution of materials therein for purposes of evaluating its anticipated performance in a particular end-use application.

It is, therefore, desired that a system including a measurement device and method for using the same be developed that is capable of providing qualitative and/or quantitative information relating to the material properties within a material microstructure of an ultra-hard construction in a manner that is not destructive. It is desired that the system and method be capable of providing such desired qualitative and/or quantitative information as it relates to a greater extent of the construction material microstructure than previously obtainable by destructive method. It is further desired that the system and method be capable of providing such qualitative and/or quantitative information in a manner having a high and consistent degree of accuracy. It is still further desired that the system and method be capable of providing such desired quantitative and/or qualitative information for constructions having material regions disposed therein that are nonplanar or nonlinear in configuration.

SUMMARY OF THE INVENTION

XRF devices, systems, and methods for using the same are disclosed herein for determining measurement characteristics, and/or providing quantitative and/or qualitative information relating to the material content and/or material microstructure of an ultra-hard construction, e.g., a ultra-hard polycrystalline construction. The ultra-hard polycrystalline body can be provided in the form of a cutting element, wherein the body is attached to a suitable substrate, and the cutting element is configured for attachment and use with a bit, e.g., for drilling subterranean earthen formations. The ultra-hard polycrystalline body can have multiple different regions, and may or may not include a catalyst material. In an example embodiment, the ultra-hard construction comprises polycrystalline diamond.

A system for determining a measurement characteristic and/or providing quantitative and/or qualitative information within a region of a diamond construction comprises the use of an X-Ray fluorescence device that is positioned adjacent the diamond construction, which can be sintered or unsintered. The device includes an emitter positioned to direct X-Ray energy onto a discrete region of the construction. The discrete region is one believed to include target elements, which target elements emit X-Ray fluorescence when contacted with the X-Ray energy. A receiver is positioned to receive the X-Ray fluorescence from the body. Means are used for determining the measurement characteristic and/or providing quantitative and/or qualitative information, relating to the discrete region of the body from the X-Ray fluorescence.

In one embodiment, the discrete region can be one that extends axially a depth from a surface of the body, and in another embodiment the discrete region can be one that extends radially inwardly from an outer surface of the body, e.g., from a cylindrical outside surface, depending on the particular measurement characteristic being evaluated. The target elements can be selected from the group of materials including those used to make the diamond body during powder assembly, constituent materials present in the substrate, and constituent materials present in a can or container used to accommodate the diamond powder assembly during HPHT sintering, and other nondiamond materials that may be intentionally or unintentionally present in the diamond body.

A feature of the XRF device, systems and methods for using the same is that they provide a tool for obtaining qualitative and/or quantitative information relating to the material content and/or material microstructure in a desired region of a polycrystalline diamond construction in a manner that is not destructive and does not result in the unwanted waste of manufactured product, that has a consistent and high degree of accuracy, that relates to a greater extent of the construction material microstructure than previously obtainable by destructive method, and that is useful as a tool for troubleshooting the possible root causes of unwanted irregularities and/or nonconformities that can be associated with powder assembly and/or the HPHT processing operation and/or equipment.

Another advantage of the inventive technique is that XRF is well-suited for examination of large numbers of parts due the capabilities of rapid elemental analysis and large sampling chambers combined with no vacuum requirements. This stands in contrast to conventional analysis techniques such as electron dispersive spectroscopy (EDS) which have comparatively long sampling times, small sampling chambers, and high vacuum requirements.

BRIEF DESCRIPTION OF THE DRAWINGS

These and other features and advantages of the present invention will be appreciated as the same becomes better understood by reference to the following detailed description when considered in connection with the accompanying drawings wherein:

FIG. 7 is a graphic illustration of a topographic plot and legend presenting information provided by X-ray fluorescence FIG. 8 is a perspective side view of an insert, for use in a roller cone or a hammer drill bit, comprising the ultra-hard polycrystalline construction evaluated using X-ray fluorescence;

FIG. 9 is a perspective side view of a roller cone drill bit comprising a number of the inserts of FIG. 8;

FIG. 10 is a perspective side view of a percussion or hammer bit comprising a number of inserts of FIG. 8;

DETAILED DESCRIPTION OF THE INVENTION

A nondestructive device and method useful for providing qualitative and/or quantitative information relating to the amount, location, and/or distribution of on or more particular target material within the material microstructure of an ultra-hard construction, e.g., an ultra-hard polycrystalline construction, according to the principles of this invention, is X-ray fluorescence (XRF). As described in better detail below, XRF is used to provide qualitative and/or quantitative information for a desired/targeted region of the ultra-hard polycrystalline construction in a manner that is accurate and that does not result in the destruction of the part.

Figure 1:
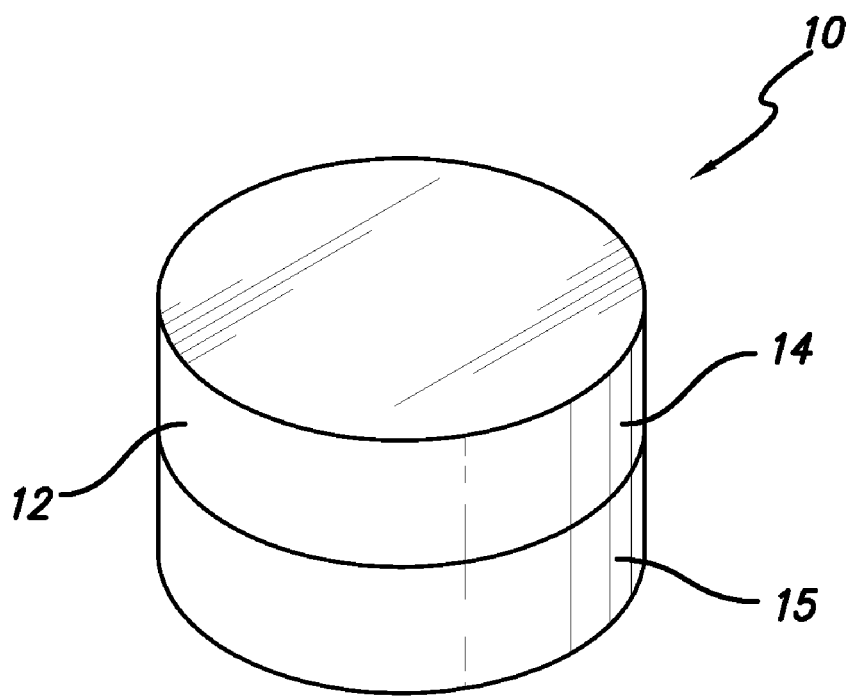
FIG. 1 is schematic view of an ultra-hard polycrystalline construction provided in the form of a compact.

FIG. 1 illustrates an example ultra-hard construction 10. Ultra-hard constructions as described herein are understood to be those that include ultra-hard materials having a hardness of greater than about 4,000 kg/mm$^2$. The construction comprises a body 12 formed from an ultra-hard polycrystalline material 14, e.g., that may comprise diamond, polycrystalline diamond (PCD), cubic boron nitride (cBN), polycrystalline cubic boron nitride (PcBN), and mixtures thereof. The body 12 may or may not be attached to a substrate. In the example embodiment illustrated in FIG. 1, the construction is shown to include substrate 15 that is joined together with the body 12 to form a compact.

The substrate may be formed from a variety of different materials such as those useful for forming conventional PCD compacts, like ceramic materials, metallic materials, cermet materials, carbides, nitrides, and mixtures thereof. When the ultra-hard polycrystalline construction comprises polycrystalline diamond, a preferred substrate material comprises cemented tungsten carbide (WC-Co).

The ultra-hard polycrystalline construction can comprise a single uniform or homogeneous material microstructure, or can comprise a material microstructure comprising multiple different regions. In such multi-region embodiment, the different regions can be located with the body in a random or ordered fashion. For example, the different regions can be provided in the form of ordered layers positioned at different depths within the body, or in the form of annular regions positioned at different radial locations within the body. Alternatively, the different regions can be randomly arranged within the body, e.g., can comprise a plurality of discrete regions that are distributed within a continuous region.

Figure 2:
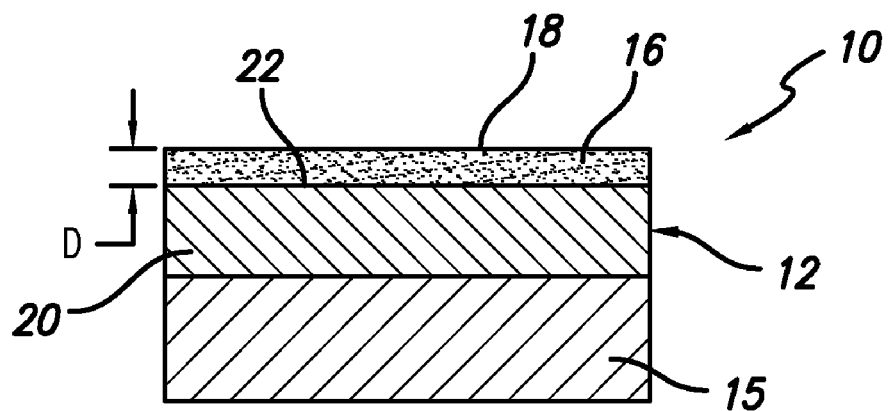
FIG. 2 is a cross-sectional side view of the ultra-hard polycrystalline construction taken along a section of FIG. 1.

FIG. 2 illustrates a cross-sectional view of a section taken through an example ultra-hard polycrystalline construction 10 comprising multiple regions. In an example embodiment, the body 12 includes a first region 16, that extends a depth "D" into the body from an outside body surface 18, and a second region 20, that extends from the first region 16 to the substrate 15. An interface 22 within the body defines the point of transition between the first and second regions 16 and 20.

In an example embodiment, the body 12 is formed from PCD and the first region 16 includes PCD that has been treated so that it is substantially free of a catalyst material used to form the PCD. As used herein, the term "substantially free" is understood to mean that the catalyst material is removed from the first region, in which case the first region has a material microstructure comprising a polycrystalline diamond matrix phase and a plurality of voids interposed therebetween. The term "substantially free" is also understood to include treatments that render the catalyst material used to form the PCD no longer catalytic, such as by reacting the catalyst material to form a noncatalytic compound and/or by encapsulating the catalyst material with another material that prevents the catalyst material from functioning as a catalyst with the polycrystalline diamond matrix phase.

The catalyst material used to form the PCD in the body can be the same as that used to form conventional PCD by high pressure/high temperature (HPHT) process, such as metals from Group VIII of the Periodic table, with cobalt (Co) being the most common. In an example embodiment, the catalyst material is a solvent metal catalyst such as Ni, Co, Fe, and combinations thereof. The catalyst material can be removed by chemical, electrical, or electrochemical processes. In an example embodiment, the catalyst material is Co and is removed by acid leaching process.

In an example embodiment, it is desired that the depth "D" of the first region within the body be controlled to provide consistent and repeatable characteristics of mechanical and thermal performance for the construction. As explained in greater detail below, it is therefore necessary to develop an accurate and repeatable technique for measuring the depth of the first region in the construction to ensure the consistency of such desired performance characteristics.

The body second region 20 comprises PCD that includes the catalyst material. The PCD region 20 has a material microstructure comprising a polycrystalline diamond matrix and the catalyst material disposed interstitially within the matrix. In an example embodiment, the substrate 15 is attached to the body 12 at the interface with the body second region 20.

The depth of the first region can be controlled by adjusting one or more parameters of the process that are used to treat the first region to render it substantially free of the catalyst material. Once a desired depth is achieved, e.g., to meet the desired performance characteristics for a particular end use application, the process is carefully controlled so that the first region depth in all remaining parts is the same.

Figure 3:
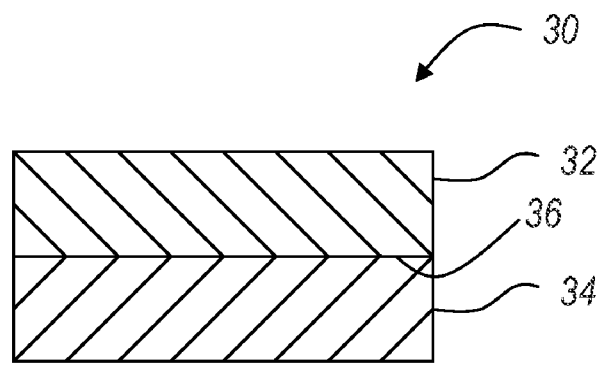
FIG. 3 is a cross-sectional side view of an alternative the ultra-hard polycrystalline construction.

FIG. 3 illustrates a cross-sectional view of a section taken through another example ultra-hard polycrystalline construction 30 comprising an ultra-hard polycrystalline diamond body 32 that is attached to a metallic substrate 34 along a body interface 36. The body 43 of this particular embodiment comprises a single region having a substantially uniform material microstructure. As used herein, the term "substantially uniform" is understood to mean that the polycrystalline matrix phase of diamond within the body is uniform, and that the amounts of other materials within the body present within the interstitial regions may vary, e.g., in gradient fashion, at different locations within the body. For example, it is understood that the amount of any constituent material of the substrate that may have infiltrated into the body during sintering may vary in content with distance within the body.

In one example embodiment, the body 32 can have a material microstructure comprising the catalyst material distributed throughout and positioned within interstitial regions within the intercrystalline diamond matrix. Alternatively, the body 32 can be one that has been treated to remove the catalyst material entirely therefrom. In which case the diamond body can be characterized as being substantially free of the catalyst material forming essentially thermally stable polycrystalline diamond (TSP). When reattached to a metallic substrate, such TSP body may include a region of a binder material adjacent the substrate that has been introduced into the diamond body.

As noted above, the use of destructive techniques to evaluate material microstructures of these constructions adversely impacts manufacturing costs and efficiency. Additionally, this process is time consuming in terms of both preparing the cut parts for visual evaluation and actually visually evaluating the parts. Thus, the use of such method on a regular basis is not practical for a large scale manufacturing processes due to both the number of parts destroyed, and the large amount of time involved in preparing and measuring each such part. Ideally, it is desired that one be able to evaluate each and every part that is made for the purpose of ensuring its performance characteristics, rather than depending on a sampling method of testing only one of a number of manufactured parts, which sampling method ultimately relies on the consistency of the manufacturing process to ensure that the remaining unsampled parts conform with the sampled one.

Further, the use of such destructive techniques were only useful for gaining knowledge of the specific cut section of the part being evaluated, and shed very little light on the remaining regions of the material microstructure, which many times represented the bulk of the construction that may play a larger role in the performance of the part when placed in the desired end-use application.

XRF is a technique that can be used to nondestructively provide qualitative and/or quantitative information relating to the material content and/or material microstructure in one or more identified regions in the body in a manner that is accurate, and that provides such information as it relates to a greater and more meaningful area of the material microstructure, thus enabling the user to better evaluate and predict performance properties for the entire construction.

Briefly, XRF relies on bombarding a desired target material with x-ray energy provided from an x-ray excitation source such as an e-ray tube or a radioactive source. Once the x-ray enters the material it is either absorbed by a target element or scattered through the material. When the x-ray is absorbed by a target element, the element transfers all of its energy to an innermost electron, which mechanism is referred to as the "photoelectric effect." During this process, if the primary x-ray has sufficient energy, electrons are ejected from the inner shells of the element, creating vacancies or voids in the vacated shells. These vacancies present an unstable condition for the element.

Electrons from the element's outer shells are transferred to the inner shells to return the element to a stable condition. The process of electron transfer from the outer shell to the inner shell produces a characteristic x-ray having an energy that is the difference between the two binding energies of the corresponding shells. The x-rays emitted by the element during this process are called X-ray fluorescence (XRF). The process of detecting and analyzing the emitted x-rays is called XRF analysis. Depending on the particular application, XRF can be produced by using not only x-rays but also other primary excitation sources like alpha particles, protons, or high-energy electron beams.

The energy level or wavelength of fluorescent x-rays emitted by the element is proportional to the atomic number relating to the target element and is characteristic for a particular material. The quantity of energy release via such emitted fluorescent x-rays is also dependent upon the thickness or depth of the material being measured.

Figure 4:
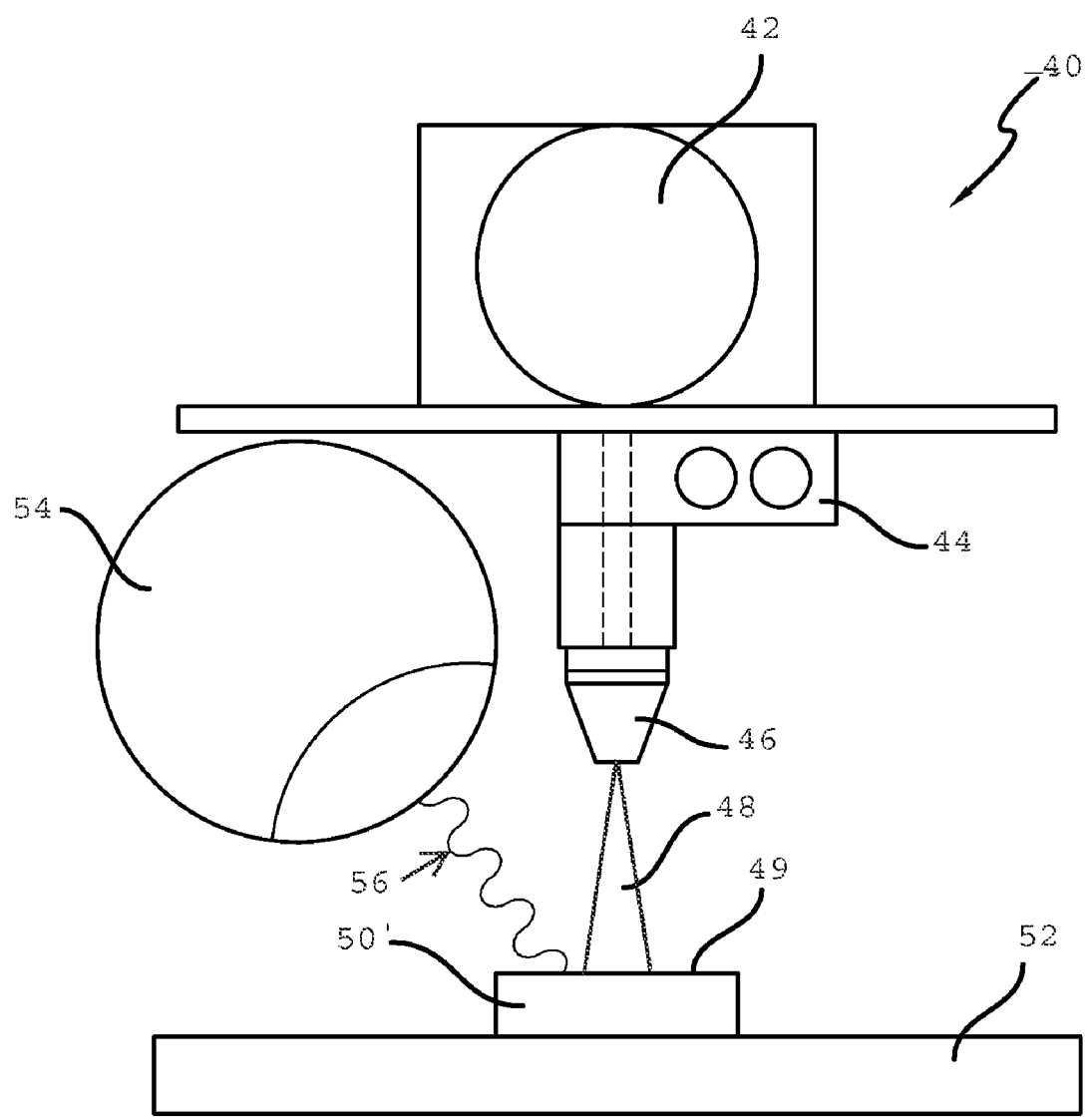
FIG. 4 is a schematic side view of an X-ray fluorescence device useful for providing qualitative and/or quantitative information relating to the material microstructure within the ultra-hard polycrystalline construction of FIGS. 1 to 3.

FIG. 4 illustrates an XRF device 40 as used to provide qualitative and/or quantitative information relating to the material microstructure of one or more regions in an ultra-hard polycrystalline construction. In an example embodiment, the device 40 comprises an x-ray source 42 and can include a fail-safe shutter 44 and a collimator 46. The collimator is used to direct an incident x-ray 48 onto a desired surface 49 of the ultra-hard polycrystalline construction 50 that is positioned on a suitable positioning assembly 52. In an example embodiment, the positioning assembly and/or the x-ray source can be configured to move if necessary to provide extended coverage over a desired region of the ultra-hard polycrystalline construction 50.

The device 40 further includes a proportional counter 54 that may be part of or separate from the device. The proportional counter may comprise a gas disposed within a counter tube, which gas is ionized by the emission of x-rays or photons from the target material. The emitted x-rays or photons 56 ionize gas in the counter tube that is proportional to their energy, permitting spectrum analysis for determining the desired qualitative and quantitative feature of the target material.

In an example embodiment, the ultra-hard polycrystalline construction 50 is oriented with the device 40 so that the device emits x-ray energy 48 onto a desired surface of the ultra-hard construction to target a desired region of the material microstructure disposed within. In one example, the construction 50 is oriented with the device 40 to emit x-ray energy 48 onto the surface 39 to provide quantitative and/or qualitative information relating to a region of the material microstructure extending from the surface a depth into the construction. It is to be understood that the construction and device can be oriented in a variety of different configurations for the purpose of obtaining qualitative and/or quantitative information as it relates to differently oriented regions of the construction microstructure.

The device can be configured having an x-ray source 42 that is specially selected to produce x-ray energy intended to create a void in the inner shell of the a desired target element. The target element can be selected from any number of the different materials known or suspected to be within the ultra-hard polycrystalline construction, and the choice may depend on the particular performance feature that is being evaluated. For example, if a performance feature being evaluated is the thermal stability of the construction, then the target element selected may be the catalyst material and the XRF device 40 is then used to provide qualitative and/or quantitative information relating to the catalyst material in the construction, e.g., for example its amount and/or location and/or distribution adjacent a working surface of the construction body.

Alternatively, it may be desired to detect the presence, amount, location, and/or distribution of any material known to be used during the processing of the raw materials used to form the ultra-hard polycrystalline construction, e.g., to evaluate the effects if any of such materials on the performance properties of the construction. For example, during the milling of the diamond grains prior to powder assembly for sintering, and steel milling jars are commonly used and trace amounts of the jar material are present in powders milled for any significant length of time. It may therefore be desirable to select iron as target element to evaluate its presence and consistency in the construction and its possible impact or contribution to the performance properties of the construction.

In an other example, the target element that is selected may be one that is present as a constituent of the substrate or other object that is in contact with the diamond volume during the HPHT sintering process. Examples of such constituent materials can include those conventionally present in metallic, ceramic, and/or cermet substrates conventionally used for making PCD constructions, e.g., tungsten and the like. Other examples of such constituent materials can include those conventionally present in the can or container that is used to accommodate the diamond powder assembly during HPHT processing, such as niobium and the like. Quantitative and qualitative information gained by XRF technique as to the presence of such materials within one or more selected regions of the construction can be useful for evaluating the effectiveness of the HPHT process, and/or the performance properties of the construction.

In another example, it may be desired to evaluate a region of the construction that can only be evaluated by sectioning the construction, in which case the construction is sectioned prior to being positioned for XRF analysis. In an example embodiment, for example where it may be desired to obtain information relating to a target element and its migration in the diamond body from the substrate, wherein the information regarding the target element can relate to that in the diamond body and/or in the substrate, it may be desired to section the construction axially. Once prepared, the sectioned portion of the construction can be positioned adjacent the XRF device to emit X-rays onto a region of the construction extending along the exposed section. Accordingly, it is to be understood that while the XRF device and method for using the same does not require destructive treatment of the object being evaluated, it can be used on such sectioned objects if information relating to a particular, e.g., not otherwise accessible, region is desired.

In another example, the target element can be one that is already present during the powder assembly of the different materials used to form the assembly for HPHT processing. Alternatively, the target element may be one that is intentionally added as a tracer to later track its position. The XRF technique can then be used to provide quantitative and/or qualitative information relating to the content or position of such selected element at a state before the powder assembly is subjected to the HPHT process to evaluate the effectiveness of the assembly process.

A feature of using the XRF technique is that because it is noninvasive, it enables a user to conduct an evaluation of the construction at different stages of manufacturing. For example, it can be used to evaluate the construction after it has been sintered, before it has been sintered and exists as a powder assembly, or at different stages of the HPHT sintering process. For example, to better understand the effects of an existing or modified HPHT process, it may be desired to conduct the HPHT process in different stages, where the XRF technique is used to provide qualitative and quantitative information relating to a selected region of the construction at each different stage, and/or after changes have been made to the HPHT process to evaluate the effects of such changes. Using the XRF technique in this manner can enable a user to perhaps make changes to the HPHT operating conditions and/or device in a manner that is calculated to provide a desired result, e.g., a more uniformly or better sintered construction likely to provide improved performance properties.

Referring to the construction illustrated in FIG. 2, in one example embodiment, the device is configured to emit x-rays onto a designated surface area of the ultra-hard polycrystalline construction to produce XRF from the targeted elements, e.g., the catalyst material in the second region, within such designated surface area. X-rays that are generated by the device pass through the ultra-hard polycrystalline construction body first region and to the target elements in the second region. The XRF emitted from the targeted elements in the portion of the second region associated with the designated surface area is measured. In an example embodiment, the XRF emitted provide information relating to an indication of the distance from the surface 34 of the ultra-hard polycrystalline construction to the second region, or the thickness or depth of the first region.

Figure 5:
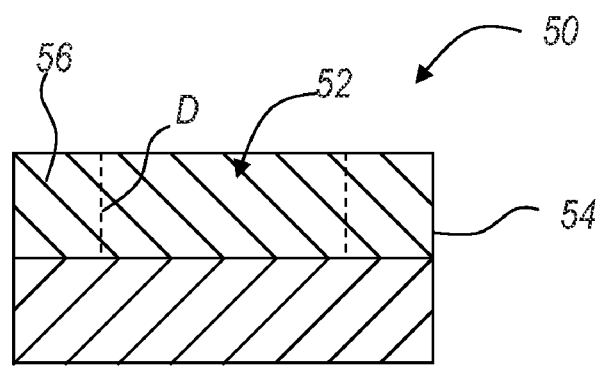
FIG. 5 is a cross-sectional side view of an ultra-hard polycrystalline construction schematically illustrating a region evaluated by X-ray fluorescence.

FIG. 5 illustrates ultra-hard polycrystalline construction 50 of FIG. 3, and use of the XRF device to emit x-rays onto a designated surface area of the ultra-hard polycrystalline body 52 to produce XRF from the desired targeted elements. In this embodiment, the x-rays are directed onto an outer cylindrical surface 54 of the body for the purpose of evaluating information relating to the target element in an annular region 54 extending radially inwardly a distance "D" therein. In an example embodiment, the target element is a constituent of the can or container used to accommodate the diamond powder assembly therein during HPHT processing. Qualitative and/or quantitative information relating to the target element in this embodiment is useful for gaining information to the HPHT operating conditions and the HPHT device, which information is useful for optimizing sintering of the construction for ensuring consistent and desired construction performance properties.

Figure 6:
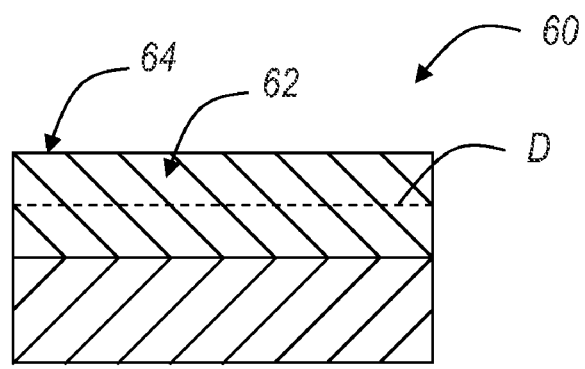
FIG. 6 is a cross-sectional side view of an ultra-hard polycrystalline construction schematically illustrating a another region evaluated by X-ray fluorescence.

FIG. 6 illustrates ultra-hard polycrystalline construction 60 of FIG. 3, and use of the XRF device to emit x-rays onto a designated surface area of the ultra-hard polycrystalline body 62 to produce XRF from the desired targeted elements. In this embodiment, the x-rays are directed onto a top surface 64 of the body for the purpose of evaluating information relating to the target element in region 64 extending axially downwardly a distance "D" therein. In an example embodiment, the target element is a constituent of the substrate that is attached to the diamond body, which attachment and infiltration of the target element can occur during the HPHT sintering process or during a subsequent HPHT process when the diamond body being attached is TSP. When the substrate being attached is WC-Co, the target element can be tungsten or cobalt. Qualitative and/or quantitative information relating to the target element in this embodiment is useful for gaining information to the HPHT operating conditions and the HPHT device, which information is useful for optimizing sintering of the construction for ensuring consistent and desired construction performance properties.

In another example embodiment, the XRF device can be used to evaluate the presence of a target element within the construction substrate before or after HPHT sintering of the ultra-hard polycrystalline body. In one example, the target element can be a constituent of the substrate and XRF can be used to provide qualitative and/or quantitative information relating to the remaining presence of this target element in the substrate after HPHT sintering, e.g., when a WC-Co substrate is used the target element can be tungsten or Co, which can be helpful for evaluating the effectiveness of such substrate and/ or the effectiveness of the HPHT process.

Means are used for determining the measurement characteristic and/or providing quantitative and/or qualitative information, relating to the discrete region of the body from the X-Ray fluorescence. Means useful in this regard can include computers, computer software, stored data and other types of data processing hardware and/or software and/or materials conventionally used for converting one type of measured data into a desired quantity and/or presenting such data or transformed data in a desired manner, e.g., in the form of a chart, table, plot or the like.

In an example embodiment, the information taken by XRF technique can be used to generate a plot of the selected region setting forth such information within such region as the amount of the target element, and the location and distribution of the target element. Generally speaking, the qualitative and/or quantitative information provided by the XRF device is helpful in identifying possible irregularities and/or nonconformities within the material microstructure that could result in poor product performance and/or product failure.

If desired, the device can be used multiple times to emit x-rays onto other surface areas of the ultra-hard polycrystalline construction to obtain desired data and plot the desired information for a greater extent of the total construction microstructure. Generally speaking, the surface area of the target material that is covered by the device in one instance will vary depending on the size of the collimator. The larger the collimator the larger the surface area capable of being covered, and the fewer number of times that the device will need to be used to generate data sufficient to cover the entire surface area of the target material, if such is desired.

In an example embodiment, it may be desired to use the XRF device to obtain data and plot the desired qualitative and/or quantitative information over an entire region of the ultra-hard polycrystalline construction. When used in this manner, the XRF device provides plotted data that can provide a topographical view of region being evaluated. Such a topographical view can be very helpful in identifying any irregularities and/or nonconformities within the region, and can be very helpful as a tool for troubleshooting and determining the root cause of such unwanted irregularities and/or nonconformities, For example, the use of such a topographical plot can help to identify whether any such irregularities are in a arranged in pattern or are random, which can be useful for the purpose of evaluating and/or controlling the process used to make the ultra-hard polycrystalline construction, e.g., whether the unwanted issues are likely to have occurred during or before powder assembly, or during the HPHT sintering process.

FIG. 7 illustrates a plot 70 that is generated by using the XRF device of FIG. 4. The plot provides a topographical visual indication of both the location and the content of a desired target element in the body. In this particular example, the target element is cobalt and a region of the body extending axially from a top surface is being evaluated. The data is generated using previously calibrated XRF counts from known depletion depth samples. As illustrated, the cobalt content varies at different locations in the body, and the different cobalt amounts are represented by differently colored region. The amounts corresponding to the differently colored regions are indicated in the legend as, moving from highest content to lowest content, 72, 74, 76, 78, 80, 82, 84 and 86.

XRF can be used to nondestructively provide qualitative and/or quantitative information of one or more regions of ultra-hard polycrystalline constructions that are configured for use in a number of different applications, such as tools for mining, cutting, machining and construction applications. Such ultra-hard polycrystalline constructions are particularly well suited for forming working, wear and/or cutting components in machine tools and drill and mining bits such as roller cone rock bits, percussion or hammer bits, diamond bits, and shear cutters.

FIG. 8 illustrates an embodiment of an ultra-hard polycrystalline construction, comprising one or more regions within the body evaluated using XRF, provided in the form of an insert 90 used in a wear or cutting application in a roller cone drill bit or percussion or hammer drill bit. For example, such inserts 90 are constructed having a substrate portion 92, formed from one or more of the substrate materials disclosed above, that is attached to a body 94 having a first and second region as described above. In this particular embodiment, the insert comprises a domed working surface 96. It is to be understood that ultra-hard polycrystalline constructions can be configured as inserts having geometries other than that specifically described above and illustrated in FIG. 8.

FIG. 9 illustrates a rotary or roller cone drill bit in the form of a rock bit 100 comprising a number of the wear or cutting inserts 90 disclosed above and illustrated in FIG. 8. The rock bit 100 comprises a body 102 having three legs 104 extending therefrom, and a roller cutter cone 106 mounted on a lower end of each leg. The inserts 90 are the same as those described above comprising the ultra-hard material construction, and are provided in the surfaces of each cutter cone 106 for bearing on a rock formation being drilled.

FIG. 10 illustrates the insert 90 described above and illustrated in FIG. 8 as used with a percussion or hammer bit 110. The hammer bit generally comprises a hollow steel body 112 having a threaded pin 114 on an end of the body for assembling the bit onto a drill string (not shown) for drilling oil wells and the like. A plurality of the inserts 90 are provided in the surface of a head 116 of the body 112 for bearing on the subterranean formation being drilled.

Figure 11:
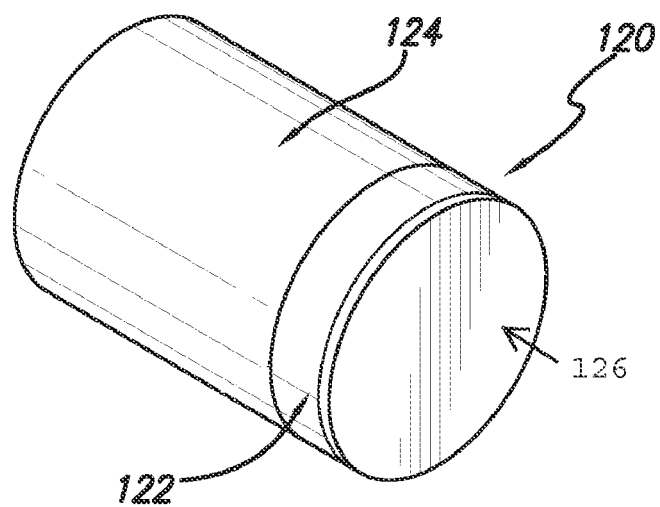
FIG. 11 is a schematic perspective side view of a diamond shear cutter comprising the ultra-hard polycrystalline construction evaluated using X-ray fluorescence.

FIG. 11 illustrates an ultra-hard polycrystalline construction evaluated using the XRF as embodied in the form of a shear cutter 120 used, for example, with a drag bit for drilling subterranean formations. The shear cutter 120 comprises a polycrystalline body 122 that is sintered or otherwise attached to a substrate 124. The body 122 includes a working or cutting surface 126. The working or cutting surface of the shear cutter can extend from the upper surface to a beveled surface defining a circumferential edge. It is to be understood that ultra-hard polycrystalline constructions can be configured as shear cutters having geometries other than that specifically described above and illustrated in FIG. 11.

Figure 12:
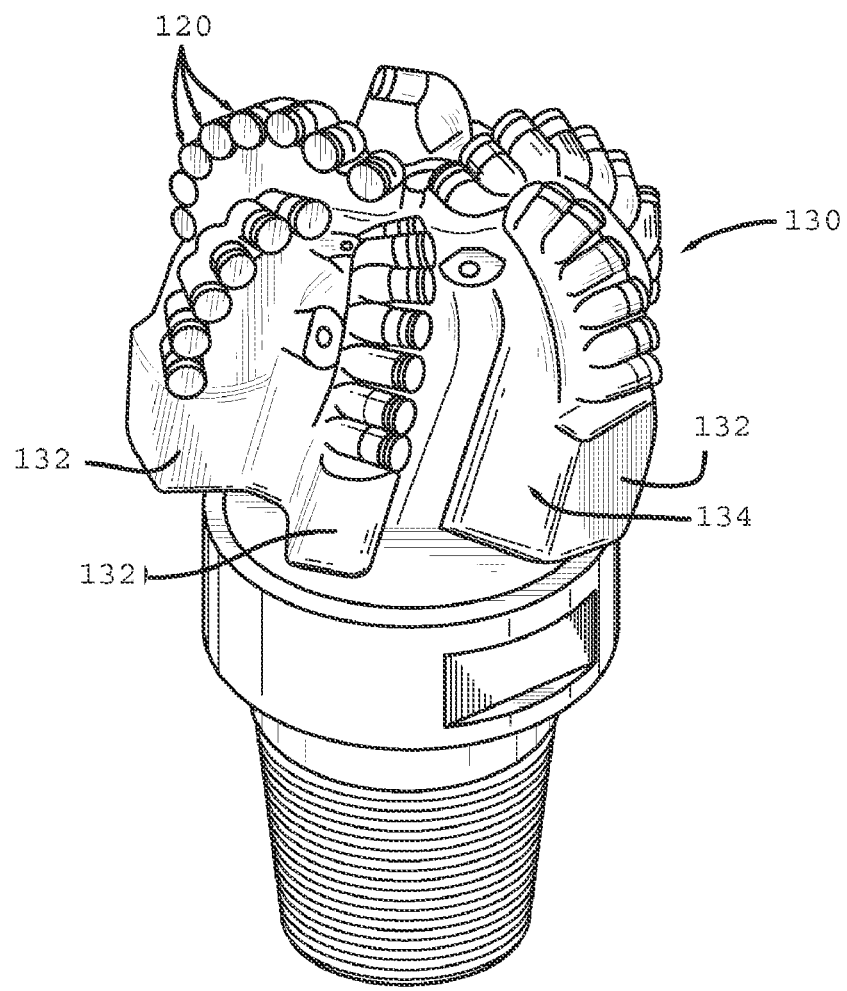
FIG. 12 is a perspective side view of a drag bit comprising a number of the shear cutters of FIG. 11.

FIG. 12 illustrates a drag bit 130 comprising a plurality of the shear cutters 120 described above and illustrated in FIG. 11. The shear cutters are each attached to blades 132 that extend from a head 134 of the drag bit for cutting against the subterranean formation being drilled. Because the shear cutters of this invention include a metallic substrate, they are attached to the blades by conventional method, such as by brazing or welding.

Other modifications and variations of using XRF devices, techniques and methods to provide qualitative and/or quantitative information relating to the materials and/or material microstructure one or more regions within an ultra-hard polycrystalline constructions will be apparent to those skilled in the art. It is, therefore, to be understood that within the scope of the appended claims, this invention may be practiced otherwise than as specifically described.

The invention claimed is:

1. A system for determining a measurement characteristic within a region of an ultra-hard construction comprising:
an ultra-hard body comprising an ultra-hard material distributed continuously throughout the body;
an X-Ray fluorescence device positioned adjacent the body and comprising:
an emitter positioned adjacent the body to direct X-Ray energy onto a discrete region of the body, wherein the discrete region comprises target elements that emit X-Ray fluorescence when contacted with the X-Ray energy; and
a receiver positioned adjacent the body to receive the X-Ray fluorescence emitted from the body; and
means for determining the measurement characteristic within the discrete region of the body from the X-Ray fluorescence;
wherein the measurement characteristic is the location and/or amount of the target elements.

2. The system as recited in claim 1 wherein the ultra-hard material has a hardness of greater than about 4,000 kg·mm$^2$.

3. The system as recited in claim 2 wherein the ultra-hard body comprises sintered polycrystalline diamond.

4. The system as recited in claim 1 wherein the body is unsintered.

5. The system as recited in claim 1 wherein the discrete region of the body is an annular region that extends radially inwardly a depth from a cylindrical outside surface of the body.

6. The system as recited in claim 1 wherein the target elements include one or more elements from a container used to house and sinter the ultra-hard material used to form the ultra-hard body during high temperature-high pressure conditions.

7. The system as recited in claim 6 wherein the target elements are selected from the group of materials consisting of niobium, tantalum, molybdenum, zirconium, hafnium and combinations thereof.

8. The system as recited in claim 1 wherein the discrete region of the body extends axially downwardly a depth from a top surface of the body.

9. The system as recited in claim 1 wherein the target elements include one or more elements selected from the group consisting of nondiamond materials mixed with an ultra-hard material before sintering, nondiamond materials combined with the ultra-hard material during sintering, and combinations thereof.

10. The system as recited in claim 1 wherein the target elements are selected from the group of binder materials consisting of Group VIII materials, Si, Ti, Cu, Ag, Au and combinations thereof.

11. The system as recited in claim 1 wherein the ultra-hard construction comprises a metallic substrate joined to the body, and wherein the target elements are selected from the group of substrate constituent materials consisting of W, Group VIII materials, C, Si, V, Cr, Mo and combinations thereof.

12. The system as recited in claim 1 wherein the ultra-hard construction comprises a metallic substrate joined to the body, and wherein the discrete region extends axially a depth into the body from a top surface of the body.

13. The system as recited in claim 1 wherein the means for determining the measurement characteristic provides a map illustrating the measurement characteristic within the discrete region.

14. A bit for drilling subterranean formations comprising a body and a number of cutting elements operatively attached to the body, wherein one or more of the cutting elements comprises the ultra-hard construction with a region evaluated according to the system as recited in claim 1.

15. A device for nondestructively determining a location or amount of target elements within an ultra-hard construction comprising an ultra-hard body, the device comprising:
- an emitter positioned adjacent the body for emitting X-ray energy onto the body and into a discrete region of the body, wherein target elements within the region emit fluorescence when contacted with the X-ray energy, and wherein the body comprises an ultra-hard material continuously dispersed throughout;
- a detector positioned adjacent the body for receiving X-ray fluorescence from the body; and
- means for determining the location or amount of target elements from the X-ray fluorescence received by the detector.

16. The device as recited in claim 15 wherein the ultra-hard body is formed from sintered polycrystalline diamond.

17. The device as recited in claim 15 wherein the body comprises unsintered diamond grains.

18. The device as recited in claim 15 wherein the discrete region comprises an annular region extending radially inwardly a depth from an outer cylindrical surface of the body.

19. The device as recited in claim 15 wherein the discrete region extends axially a depth into the body from a top surface of the body.

20. The device as recited in claim 15 where the ultra-hard construction comprises a metallic substrate attached to the body, and wherein the discrete region extends axially a depth in the body from an interface with the substrate.

21. The device as recited in claim 20 wherein the discrete region extends axially from the substrate to a top surface of the body.

22. The device as recited in claim 15 further comprising means for generating a map illustrating the location or amount of target elements within the discrete region.

23. A bit for drilling subterranean formations comprising a body and a number of cutting elements operatively attached to the body, wherein one or more of the cutting elements comprises the ultra-hard construction with a region evaluated using the device as recited in claim 15.

24. A method for nondestructively determining a characteristic feature within a region of an ultra-hard construction comprising an ultra-hard body; the method comprising the steps of:
- directing X-ray energy onto a surface of the body into a discrete region of the body, wherein the body comprises an ultra-hard material that is continuously distributed throughout;
- receiving X-ray fluorescence emitted from target elements within the discrete region; and
- determining from the received X-ray fluorescence the characteristic feature within the discrete region;
- wherein the characteristic feature is the location and/or amount of the target elements.

25. The method as recited in claim 24 wherein the ultra-hard body comprises unsintered diamond grains.

26. The method as recited in claim 24 wherein the ultra-hard body is formed from sintered polycrystalline diamond.

27. The method as recited in claim 24 wherein the discrete region extends radially a distance into the ultra-hard body from an outside surface.

28. The method as recited in claim 24 wherein the discrete region extends axially a depth into the body from a top surface.

29. The method as recited in claim 24 wherein the ultra-hard construction comprises a metallic substrate attached to the ultra-hard body, and wherein the discrete region extends axially a depth in the body from an interface with the substrate.

30. A bit for drilling subterranean formations comprising a body and a number of cutting elements operatively attached to the body, wherein at least one cutting element comprises the ultra-hard body having a region evaluated according to the method as recited in claim 24.

* * * * *